United States Patent

Barnes et al.

[11] Patent Number: 5,402,062
[45] Date of Patent: Mar. 28, 1995

[54] MECHANICAL CAPTURE OF COUNT WAFER FOR PARTICLE ANALYSIS

[75] Inventors: Thomas L. Barnes, Sunrise; James W. Colburn, Margate; Catherine L. Danial, Coconut Creek, all of Fla.; Sangvorn Rutnarak, Long Grove, Ill.

[73] Assignee: Abbott Laboratories, Abbott Park, Ill.

[21] Appl. No.: 173,735

[22] Filed: Dec. 23, 1993

[51] Int. Cl.⁶ .................... G01N 15/06; G01N 27/06
[52] U.S. Cl. .................................................. 324/71.4
[58] Field of Search .................. 73/61.71; 324/71.1, 324/71.4; 422/73

[56] References Cited

U.S. PATENT DOCUMENTS

| | | | |
|---|---|---|---|
| 3,122,431 | 2/1964 | Coulter et al. | 65/36 |
| 3,266,526 | 8/1966 | Berg | 138/103 |
| 3,361,965 | 1/1968 | Coulter et al. | 324/71 |
| 3,395,343 | 7/1968 | Morgan et al. | 324/71 |
| 3,395,344 | 7/1968 | Bader | 324/71 |
| 3,444,464 | 5/1969 | Coulter et al. | 324/71 |
| 3,515,884 | 6/1970 | Imadate | 250/218 |
| 3,539,919 | 11/1970 | Hogg | 324/71 |
| 3,554,037 | 1/1971 | Berg | 73/422 |
| 3,614,607 | 10/1971 | Schoen | 324/71 |
| 3,628,140 | 12/1971 | Hogg et al. | 324/71 |
| 3,638,677 | 2/1972 | Baccarini | 137/576 |
| 3,648,158 | 3/1972 | Parker | 324/71 |
| 3,714,565 | 1/1973 | Coulter et al. | 324/71 |
| 3,739,258 | 6/1973 | Karuhn et al. | 324/71 |
| 3,746,976 | 7/1973 | Hogg | 324/71 |
| 3,771,058 | 11/1973 | Hogg | 324/71 |
| 3,783,376 | 1/1974 | Doniguian | 324/71 |
| 3,859,012 | 1/1975 | Hogg | 417/437 |
| 3,864,628 | 2/1975 | Klass et al. | 324/71 |
| 3,902,115 | 8/1975 | Hogg et al. | 324/71 |
| 3,939,409 | 2/1976 | Hogg | 324/71 |
| 3,958,177 | 5/1976 | Reeves et al. | 324/71 |
| 3,976,429 | 8/1976 | Ginsberg | 23/259 |
| 4,014,611 | 3/1977 | Simpson et al. | 356/72 |
| 4,140,966 | 2/1979 | Godin et al. | 324/71 |
| 4,157,498 | 6/1979 | Johnson | 324/71 |
| 4,325,913 | 4/1982 | Wardlaw | 422/100 |
| 4,395,676 | 7/1983 | Hollinger et al. | 324/71 |
| 4,484,134 | 11/1984 | Halloran | 324/71 |
| 4,491,786 | 1/1985 | Godin | 324/71.1 |
| 4,710,021 | 12/1987 | Von Behrens | 356/72 |
| 4,730,155 | 3/1988 | Hogg | 324/71 |
| 4,760,328 | 7/1988 | Groves | 324/71 |
| 4,853,618 | 8/1989 | Holley | 324/71 |
| 5,007,296 | 4/1991 | Hukuhara | 324/71.4 |
| 5,094,818 | 3/1992 | Longman et al. | 324/71.4 |

*Primary Examiner*—Hezron E. Williams
*Assistant Examiner*—Michael J. Brock
*Attorney, Agent, or Firm*—Mark C. Bach

[57] ABSTRACT

A particle count probe comprises a wafer having an aperture. A first member is provided having a fluid passageway. A second member is removably mounted to the first member, and cooperates with the first member and the wafer to position the wafer so that the aperture of the wafer aligns with the fluid passageway.

10 Claims, 7 Drawing Sheets

MECHANICAL CAPTURE OF COUNT WAFER FOR PARTICLE ANALYSIS

FIELD OF THE INVENTION

Embodiments of the present invention are directed to the field of particle analysis systems and, in particular, to apparatus and methods for mounting a count wafer on a probe assembly.

DESCRIPTION OF THE PRIOR ART

In the particle analysis field, analysis of liquid samples may involve aspiration of liquid from a sample through a conduit having a metered aperture at an immersed end. A typical particle analyzer includes three basic components: a sample vessel, a liquid flow system, and a sensor. U.S. Pat. No. 5,094,818 to Longman et al., issued 10 Mar., 1992, which is incorporated herein by reference, describes one type of particle analyzer. The particle analyzer moves suspended biological or industrial particles from the sample vessel to the sensor via the liquid flow system. The suspended particles are moved through the sensor, and the sensor detects, counts and sizes the particles.

There are many types of sensors. Impedance sensors detect the change in resistance of an aperture as a particle passes through the aperture. The aperture is constructed such that particles pass through the aperture substantially one at a time.

Impedance sensors generally include a probe assembly with a count wafer. The probe assembly has a counterbore in which the count wafer is mounted. The count wafer is held in place by adhesive materials such as glue and the like. Using an adhesive to mount the count wafer to the probe assembly may create several problems. The material comprising the wafer and the probe material are different such that the adhesive is unable to hold the count wafer properly in place. Subsequently, the adhesive bond may fail.

The adhesive joint must survive under pressure in an immersed environment. Under these conditions, adhesives may fail with an adhesion failure. An adhesion failure occurs between the adhesive and the substrate. An impedance sensor has at least two substrates: the count wafer and the probe assembly. Additionally, there is a relatively small surface area on the sensor which is available for the adhesive. Because the available surface area is so small, it is extremely sensitive to surface preparation and proper mixing of the adhesive so it remains air and moisture free. In addition, using an adhesive to mount the count wafer to the probe assembly may reduce the flexibility of the overall system. For example, once the count wafer is mounted, the wafer cannot be removed, such as for cleaning or replacement by another wafer having either the same size or a different size aperture.

It is desirable to provide a method of mounting a count wafer to a probe assembly which provides increased flexibility. A particle analyzer with a removable count wafer may allow both the wafer and the internal structure of the probe assembly to be cleaned with relative ease. In addition, such a construction would allow count wafers to be replaced with another wafer if necessary.

SUMMARY OF THE INVENTION

A particle count probe comprises a wafer having an aperture. A first member is provided having a fluid passageway. A second member is removably mounted to the first member, and cooperates with the first member and the wafer to position the wafer so that the aperture of the wafer aligns with the fluid passageway.

DETAILED DESCRIPTION OF THE PREFERRED EMBODIMENTS

Figure 1:
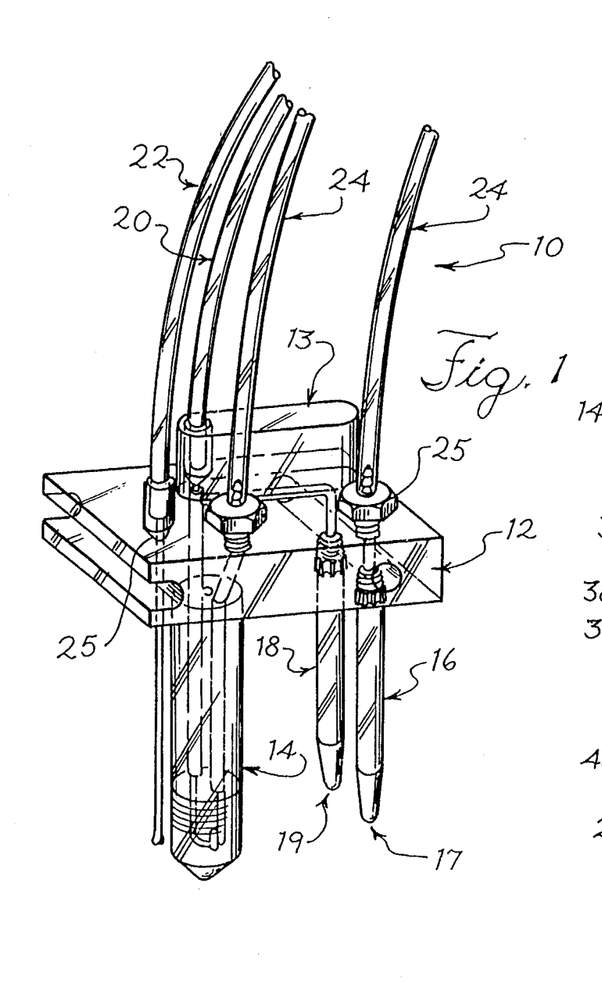
FIG. 1 illustrates a probe assembly according to a first preferred embodiment of the present invention.

FIG. 1 illustrates a probe assembly according to a first preferred embodiment of the present invention. The probe assembly 10 includes a base 12, a plug 13, count probe 14, a waste probe 16, a fill probe 18, electrodes 20 and 22, connection tubing 24 and connection fitting 25. The assembly 10 is used in conjunction with a vessel (not shown) having two separate reservoirs. In one application, a sample, such as a biological or industrial suspension of particles to be analyzed, is contained in one reservoir while the other reservoir contains a reagent solution. Depending on the type of analysis to be performed, the sample may be treated before being added to the reservoir. When the reservoirs are filled with their respective solutions, the reservoirs are raised to the probe assembly 10 so that the count probe 14 aligns with the reservoir containing the sample to be analyzed and the waste and fill probes 16 and 18 align with the reservoir containing the reagent solution. The remaining portion of the assembly 10, including the base 12 and plug 13 is not immersed in the vessel. Individual components of the probe assembly 10 will now be described in detail with reference to FIGS. 2–13.

Figures 2, 3, 4:
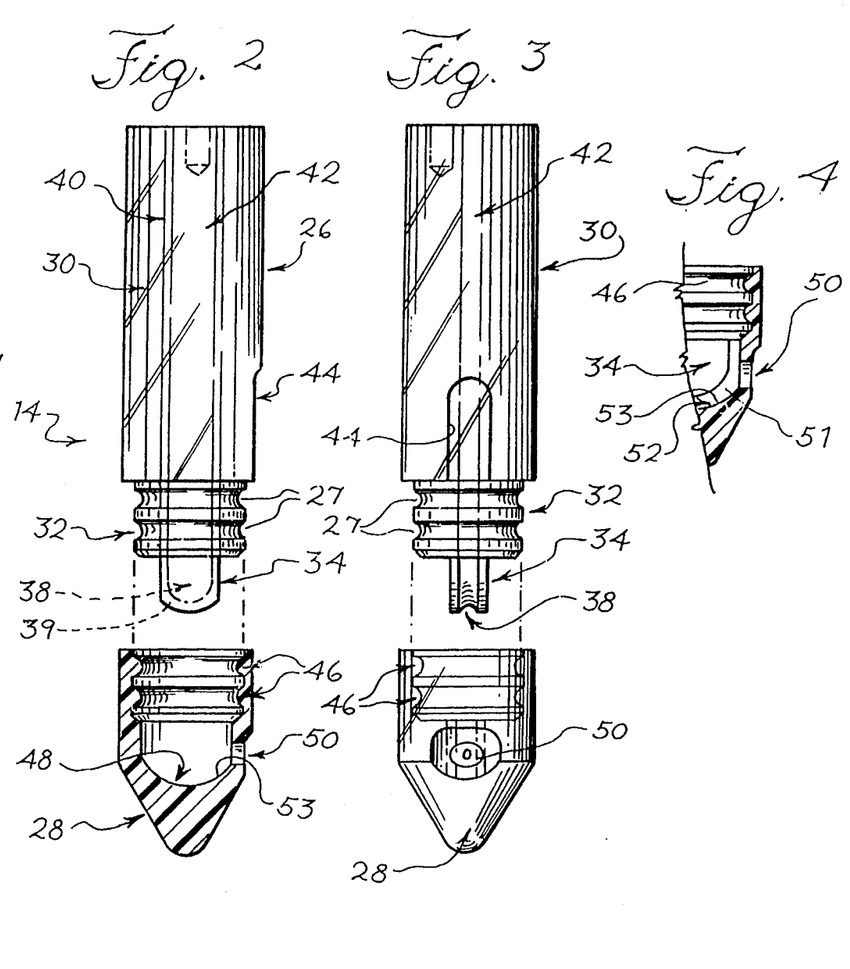
FIG. 2 illustrates a side view of the probe assembly shown in FIG. 1.
FIG. 3 illustrates a front view of the probe assembly shown in FIG. 1.
FIG. 4 illustrates a cross-sectional view of a portion of an aperture cap of the probe assembly shown in FIGS. 2 and 3.

FIGS. 2 and 3 illustrate a side view and a front view, respectively, of count probe 14. The count probe 14 comprises two components, an aperture tube 26 and a removable aperture cap 28. The cap 28 is illustrated as removed from an end of the aperture tube 26 to better illustrate each component. The aperture tube 26 will first be described in detail followed by a detailed description of the aperture cap 28.

The aperture tube 26 has three main sections: a main body section 30, a reduced section 32 and a tip section 34. The aperture tube 26 may be formed as a single piece or from separate sections bonded together by suitable means. The main body 30 and reduced section 32 are cylindrical in shape while the tip section 34 is not. In an exemplary embodiment, some dimensions of the aperture tube 26 are:

—Overall Length: 1.358 inches
—Main body section 30 diameter: 0.392 inches
—Reduced section 32 length: 0.209 inches A flat 44 is formed on an exterior surface of the main body section 30 of the tube 26. The flat 44 is used to align the aperture cap 28 with the aperture tube 26.

Grooves 27 are formed on the exterior of the reduced section 32. These grooves 27 mate with protuberances on the interior of the aperture cap 28 to secure the cap 28 to the aperture tube 26. A seal is formed between the grooves 26 and the protuberances. This seal permits no more than about 100 nanoamps of electrical current leakage at about 9 Volts through the seal formed between reduced section 32 and protuberances 46.

The tip section 34 as seen from the side view (FIG. 2) has a substantially "U" shaped latitudinal cross section. A groove 38, shown by dashed line 39 in FIG. 2 and more clearly illustrated in FIG. 3, is disposed at an end of the tip section 34. Preferably, the groove 38 has a radius of curvature of about 0.03 inches. The groove 38 mates with an interior of the aperture cap 28 to form a channel wall as will be described in detail with reference to FIG. 13.

Formed within and extending through the main body and reduced sections 30 and 32 of the tube 26 are two conduits 40 and 42, represented by dashed lines. The tip section 34 extends between depending openings of conduits 40 and 42 so that the groove 38 formed in the tip section 34 forms a continuation of a half of each conduit 40 and 42. Opposite ends of conduits 40 and 42 align with other conduits (not shown) formed in the base 12. The depending ends of conduits 40 and 42 align with a substantially "U" shaped conduit formed by the tip section 34 of the tube 26 and the interior of the aperture cap 28.

The aperture cap 28 will now be described with reference to FIGS. 2, 3 and 4. In an exemplary embodiment, the cap 28 is formed of a polymeric material, such as a molded silicone commercially available from Mobay under the name Mobay 2070 LSR Clear. Other materials, such as Silastic 80 Durometer available from Dow Corning, may also be used. In the exemplary embodiment, the cap 28 has a length of about 0.603 inches. The interior of the aperture cap 28 fits over the reduced section 32 and the tip section 34 of the aperture tube 26.

Protuberances 46, complementary in shape to the grooves 27 formed on the reduced section 32 of the tube 26, are formed on the interior surface of the cap 28. The protuberances 46 mate with grooves 27 formed on the aperture tube 26 to secure the cap 28 to the end of the aperture tube 26. As shown in FIGS. 2 and 3, a substantially "U" shaped cavity 48 is formed in the cap 28 to accommodate the tip section 34 of the aperture tube 26. Extending through a side wall of the cap 28 and into the substantially "U" shaped cavity 48 is an opening 50. The opening 50 is properly dimensioned to mount a count wafer (not shown) therein. In an exemplary embodiment, the opening 50 has a diameter substantially within the range of about 0.057 inches to about 0.067 inches and a center of the opening 50 is located about 0.304 inches from an open end or top of the cap 28.

FIG. 4 illustrates in detail a cross-sectional view of the opening 50 formed in the cap 28 to illustrate particular dimensional characteristics associated therewith. The thickness of the cap wall through which the opening 50 is formed, in the illustrated embodiment, is about 0.03 inches. It has been found that a polymeric material, such as silicone and the like, is a suitable material to form the cap 28 because a count wafer 54 (FIG. 6) can be mounted in the opening 50 and secured therein by forces exerted by the cap 28 to create an interference fit. The seal created by the interference fit should allow no more than about 100 nanoamps of electrical current leakage at about 9 Volts through the seal created between cap 28 and count wafer 54.

The forces exerted by the cap 28 to hold the count wafer 54 in place must be great enough to withstand pressure exerted on the count wafer 54 by the liquid flow system. The system typically exerts about 12 psi maximum pressure and about 3 psi maximum vacuum. The cap 28 is designed to withstand approximately 24 psi of pressure or vacuum while still retaining the count wafer 54 at the opening 50 and maintaining the above-mentioned electrical properties (i.e., current leakage).

The substantially U-shaped cavity formed in the aperture cap 28 has a trough 52. A transition area 53 is provided in trough 52. The transition area 53 does not have a constant diameter. Specifically, the transition area 53 extends from the bottom of the opening 50 to the trough 52 and is made tangent to the trough 52 substantially within the 76° range. The transition area 53 increases the cross sectional area of a fluid flow channel formed between the tip section 34 of the tube 26 and the opening 50. Area 53 allows a rear side of the count wafer 54 to lie substantially flush with the fill flow. Therefore, the fill flow is in contact with and can wash the rear side of the count wafer 54, thereby reducing the probability that bubbles might collect in the sensing region during analysis. Also, area 53 provides significant advantages to the flow geometry of the probe 10. To reduce the number of particles counted twice (recirculators), a jet of the fluid entering the count probe 14 through the count aperture should be controlled. By positioning the count wafer 54 adjacent the transition area 53, the jet of fluid through the count aperture can contact the channel wall in such a way as to be deflected away from the count aperture.

Figures 5, 6, 11, 12, 13:
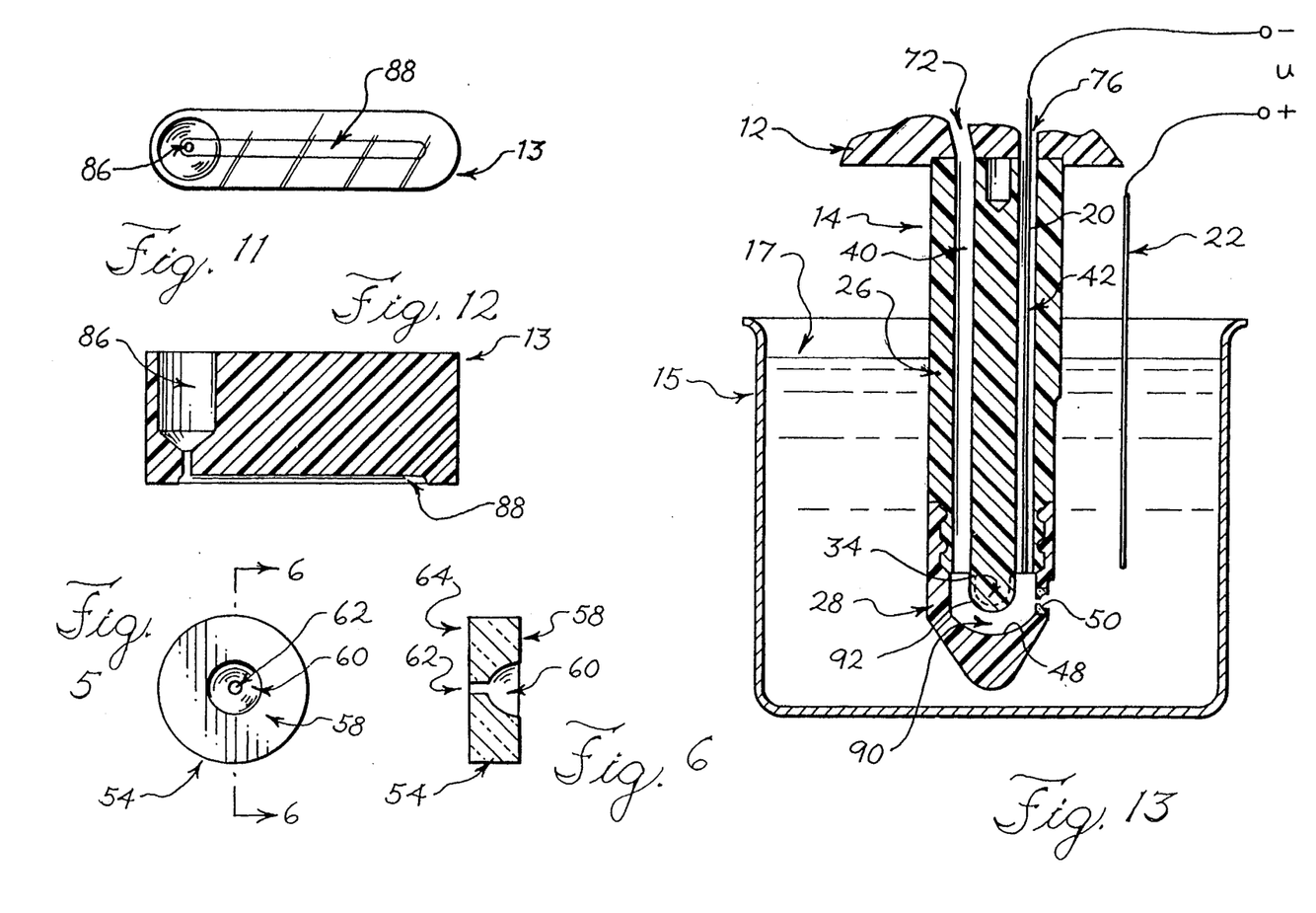
FIG. 5 illustrates a front view of a count wafer which may be used with the probe assembly of FIG. 1.
FIG. 6 illustrates a cross-sectional view of the count wafer shown in FIG. 5 taken along lines 6—6.
FIG. 11 illustrates a top view of a plug of the counting apparatus shown in FIG. 1.
FIG. 12 is a cross-sectional view of the plug shown in FIG. 11.
FIG. 13 illustrates a cross-sectional view of a count probe of the counting apparatus shown in FIG. 1 immersed in a reservoir containing a liquid suspension of particles to be analyzed.
Figure 7:
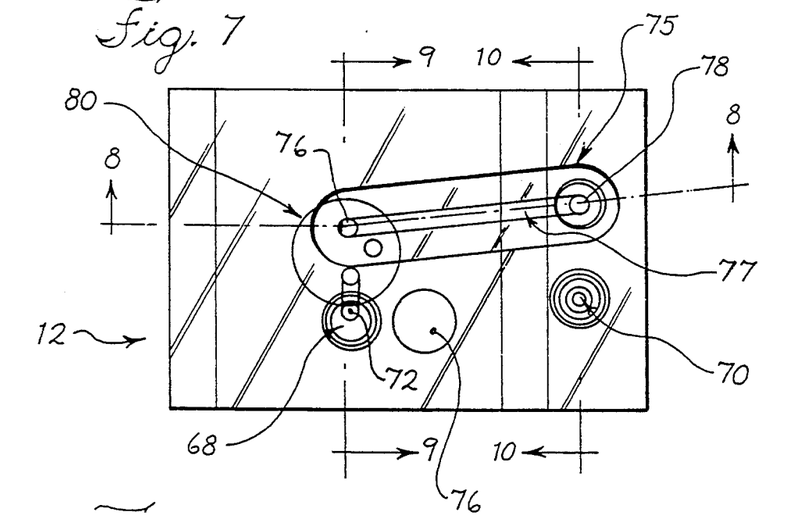
FIG. 7 illustrates a top view of base of the counting apparatus shown in FIG. 1.
Figure 9:
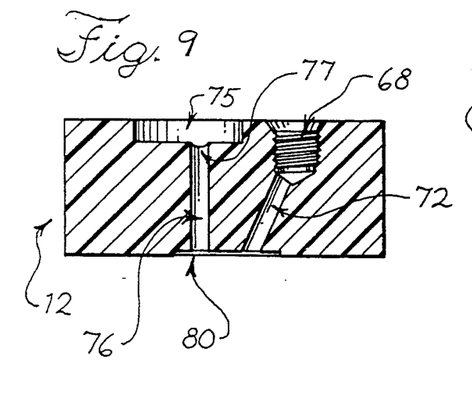
FIG. 9 is a cross-sectional view of base 12 of FIG. 7 taken along lines 9—9.
Figure 10:
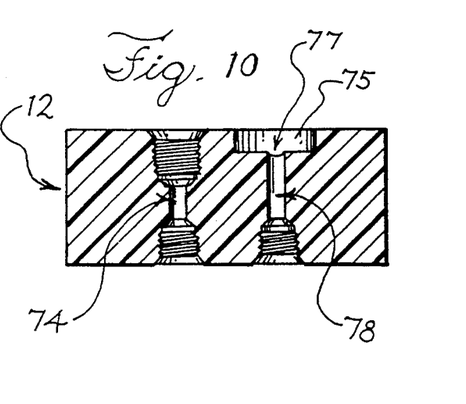
FIG. 10 is a cross-sectional view of base 12 of FIG. 7 taken along lines 10—10.

FIG. 5 illustrates a front view of a count wafer 54 which may be mounted in the opening of the cap 28 of the count probe 14. FIG. 6 illustrates a cross-sectional view of the count wafer 54 shown in FIG. 5 taken along lines 6—6. In an exemplary embodiment, the dimensions of the count wafer 54 may be approximately as follows:
- Outer diameter: 0.087 inches
- Thickness: 0.025 inches
- Concave recess 60 diameter: 0.060 inches Located at the center of the concave recess 60 is the count aperture 62 which extends through to the rear side or face 64 of the count wafer 54. The diameter of aperture 62 is chosen dependent upon the diameter of the cell type to be counted. In an exemplary embodiment, the count aperture 62 contained in the count wafer 54 may be chosen to have the following dimensions in the given situations:
- Diameter of the count aperture 62 for red blood cells and platelets: about 45 micrometers
- Length of the count aperture 62 for red blood cells and platelets: about 60 micrometers
- Diameter of the count aperture 62 for white blood cells: about 100 micrometers
- Length of the count aperture 62 for white blood cells: about 70 micrometers The count, waste and fill probes 14, 16 and 18 are all connected to base 12 as illustrated in FIG. 1. FIGS. 7-10 illustrate the base 12 in greater detail. FIG. 7 illustrates a top view of the base 12. The base 12 is preferably formed of a solid acrylic block substantially rectangular in shape. Two ports 68 and 70 expose conduits 72 and 74 (see FIGS. 9 and 10) to the top surface of the base 12. The ports 68 and 70 allow the connection tubing 24 shown in FIG. 1 to communicate with conduits 72 and 74. The ports 68 and 70 are preferably threaded as shown in FIGS. 9 and 10 to allow the connection fitting 25 (see FIG. 1) to be threadibly engaged in place on the base 12. One end of the connection tubing 24 is then connected to the fitting 25. A third port 76 allows an electrode, not shown, and fluid to pass through the base 12. Unlike ports 68 and 70, port 76 may not be threaded. Other conduits may be formed in the base 12 and connections between those conduits and the rest of the probe assembly 10 will be better understood with reference to FIGS. 1 and 8-12.

Figure 8:
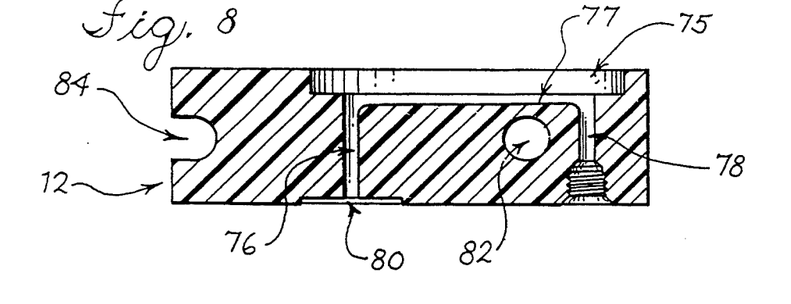
FIG. 8 is a cross-sectional view of base 12 of FIG. 7 taken along lines 8—8.

FIG. 8 is a cross-sectional view of the base 12 of FIG. 7 taken along lines 8—8. A substantially horizontal recess 75 is formed at the top of the base 12 including a conduit 77. Two conduits 76 and 78 extend vertically through the base 12 and are connected near the top of the base 12 by the horizontal conduit 77. Conduit 77 is illustrated in an "open" state. However, when the base plug (not shown) to be described with reference to FIGS. 11 and 12 is mounted in the recess 75 of the base 12, conduit 77 will be in a substantially "closed" state. In the closed state, the conduit 77 allows for connection with the conduits 76 and 78. The bottom of conduit 78 is preferably threaded to allow the fill probe 18 of FIG. 1 to be threadibly mounted on the base 12 in alignment with conduit 78. A recess 80 configured for facilitating mounting of the count probe 14 is formed on the bottom of the base 12. The recess 80 is positioned to align conduits 40 and 42 of the count probe 14 with conduits 72 and 76 (see FIG. 7) of the base 12, as will be described in detail hereinafter. An aperture 82 and "U" shaped recess 84 extend substantially horizontally through the base 12 to accommodate mounting of the probe assembly 10. Any appropriate system, such as automatic as well as manual systems, can be used to move the probe assembly 10 to various positions and locations. Because the translating mechanism forms no part of the present invention and therefore will not be described in detail.

FIG. 9 is a cross-sectional view of the base 12 of FIG. 7 taken along lines 9—9. Conduit 72 is angled towards conduit 76 so that both conduits communicate with recess 80. The count probe 14 is mounted in recess 80 so that conduit 40 of the probe 14 aligns with conduit 72 of the base 12 and conduit 42 of the probe 14 aligns with conduit 76 of the base 12, as shown in FIG. 13.

FIG. 10 is a cross-section view of the base 12 of FIG. 7 taken along lines 10—10. As previously described, conduit 78 aligns with conduit 77 in the base 12. The bottom of conduit 78 is preferably threaded so that the fill probe 18, shown in FIG. 1, can be threadibly mounted to base 12. Both end portions of conduit 74 are threaded so that the waste probe 16 can be connected to one end of conduit 74 and a connection fitting 25, shown in FIG. 1, can be connected to the opposite end of conduit 74. Connection tubing 24 can be connected to the connection fitting 25 to communicate with conduit 74.

FIGS. 11 and 12 illustrate a plan and a cross-sectional view, respectively, of the base plug 13. The plug 13 is configured to fit within the recess 75 formed in the top of the base 12, as shown in FIG. 1. Extending through the plug 13 is a conduit 86 which aligns with a recess 88 also formed in the plug 13. When the plug 13 is mounted in the recess 75 of the base 12, the recess 88 formed in the plug 13 cooperates with the conduit 77 formed in the base 12 to form a conduit connecting the conduits 76 and 78 in the base 12. When the plug 13 is mounted on the base 12, conduit 86 communicates with conduit 76 in the base 12. Conduit 76, in turn, communicates with conduit 42 of the count probe 14. In an exemplary embodiment, plug 13 is solvent bonded to the base 12. As shown in FIG. 1 and 13, electrode 20 is inserted through conduit 86 in the plug 13 and extends through conduit 42 of the probe 14. When positioned for operation, the electrode 20 is located adjacent a distal opening of conduit 42 of tube 26 so that a distal end of the electrode 20 is adjacent opening 50 when aperture cap 28 is assembled with tube 26. Conduit 86 is preferably substantially funnel-shaped so that a distal diameter of the conduit 86 is substantially smaller than the diameter of the remainder of the conduit 86. The electrode 20 has a diameter which is slightly smaller than the distal diameter of conduit 86. The adhesive may move along the electrode 20 towards the reduced diameter portion of conduit 86 to substantially reduce fluid leaking through conduit 86. The electrode 20 is preferably sealingly secured to the plug 13 by a suitable structure, such as an adhesive and the like. The adhesive may be a polymeric compound, such as Armstrong Epoxy A251 and the like.

FIG. 13 illustrates a cross-sectional view of a portion of the probe assembly 10 in use. The count probe 14 is shown at least partially submerged in a reservoir 15 containing a liquid suspension 17 of particles to be analyzed. With the aperture cap 28 secured to the end of the tube 26, conduits 40 and 42 formed in the tube 26 are connected by a conduit 90 formed between the tip section 34 of the tube 26 and the interior cavity 48 of the cap 28 (FIG. 2). A groove in the tip section 34, illustrated by dashed line 92, forms a channel wall. In an exemplary embodiment, with the exception of the transition area 53, the conduits are typically of a constant diameter of about 0.060 inches.

As previously described, conduit 42 is connected with conduit 76 in the base 12 and thus is connected by conduit 77 to conduit 76, which is connected to the fill probe 18. In addition, electrode 20 is positioned in conduit 42 through conduits 86 and 76 of the base plug 13 and base 12, respectively. The conduit 40 of the count probe 14 communicates with connection tubing 24 through conduit 72 of the base 12.

Referring to both FIGS. 1 and 13, the operation of the particle analyzer will now be described.

During the counting phase of the analytical cycle a vessel, which may have a sample and a reagent reservoir, is positioned to at least partially submerge the probes 14, 16 and 18 of assembly 10 in the fluids contained in the vessel. A suitable vessel is described in U.S. patent application, Ser. No. 07/482,007 entitled "Self-Filling, Anti-Siphon Fluid Flow System for Particle Analysis Instruments and a Disposable Reagent Pack for use Therewith", filed Feb. 16, 1990, which is incorporated herein by reference. Other vessels may also be appropriate.

Once the probes 14, 16 and 18 of assembly 10 have been sufficiently submerged in the fluids contained in the vessel, the analytical cycle of the system may be started. In an exemplary embodiment, both the fill and waste probes 18 and 16 have apertures 19 and 17 respectively, (see FIG. 1) which are approximately 203 micrometers in diameter. Fluid enters through the fill aperture 19 in the fill probe 18 from the reagent reservoir. This fluid movement may be generated by a suitable mechanism, such as a fluid displacement mechanism pulling at a constant flow rate and the like. The reagent solution is supplied to conduit 42 of the count probe 14 through conduits 77 and 78 where the reagent solution mixes with the sample liquid. Suspended particles enter through the count aperture 62 of the count wafer 54. A voltage potential is applied between electrode 20 placed in conduit 42 of the count probe 14 and electrode 22 disposed in the sample reservoir 15 to cause a current to flow through the adjacent fluid. Appropriate electronics (not shown) are provided for detecting a change in voltage when a cell passes through the count aperture 62 of the count wafer 54. Each passing cell causes an electronically recorded cell count to increase. The constant flow rate displacement mechanism generates a negative pressure in conduit 40 of the count probe 14 and fill aperture 19. The negative pressure is predetermined such that a desired rate of fluid flow is maintained through the count aperture 62. As particles enter the count probe 14 through the count aperture 62, they mix with the fluid flowing in conduit 42 thereby causing the particles to flow around the conduit 90 formed between the tip section 34 and cap 28.

During the count phase, a valve, not shown, is activated to prevent fluid from entering through the waste aperture 17 in the waste probe 16. When the counting phase is complete, flow is reversed, for example, by reversing the constant flow rate displacement mechanism (not shown). The fluid displacement mechanism collects the diluted sample. The displacement mechanism then expels the collected sample back out the probe assembly 10 to the reagent reservoir before accessing the next sample. Preferably, the expel cycle delivers waste out the probe assembly 10 at approximately twice the flow rate of the sampling cycle. Waste leaves the probe assembly 10 through the waste probe 16, the fill probe 18, and the count aperture 62. Then, the valve to the waste probe 16 closed. Therefore, the flow rate out of the fill probe 18 and the count aperture 62 is increased by a factor, preferably about two. These steps substantially clean the apertures of any debris. For red blood cell and platelet counting, the fill, count and waste apertures may have diameters, for example of 203, 45, and 203 micrometers, respectively. For white cell counting, the same diameters may be, for example, 203, 100 and 203 micrometers, respectively.

The count probe 14 of FIG. 1 offers several advantages. Cap 28 and count wafer 54 are removable for facilitating cleaning of the aperture tube 26 and cap 28. Defective or worn elements can also be replaced, and the count wafer can be exchanged for another having a different aperture size.

Figure 14:
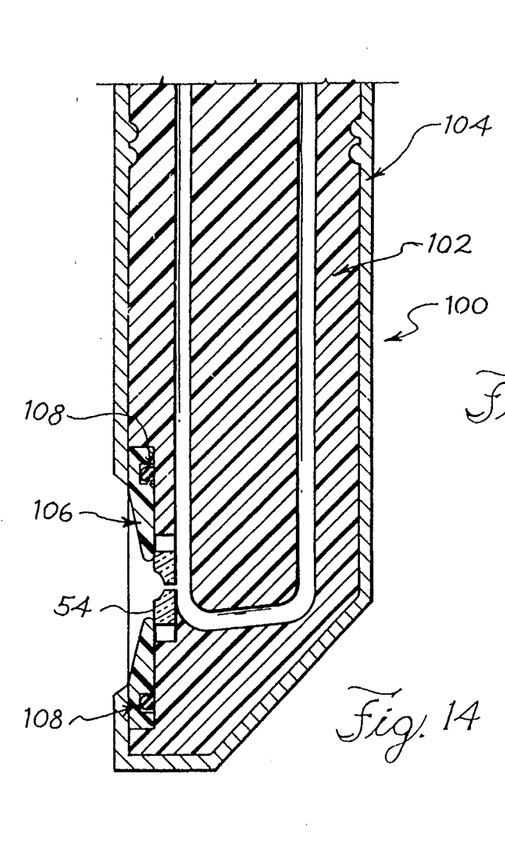
FIG. 14 illustrates a count probe assembly according to a second preferred embodiment of the present invention.

A second preferred embodiment of the present invention will now be described with reference to FIGS. 14–27. FIG. 14 illustrates a count probe assembly 100. The probe assembly 100 includes at least five members: a core member 102, a sleeve member 104, an aperture count wafer plate 106, an O-ring 108 and a count wafer 54. In this embodiment, the count wafer plate 106 houses the count wafer 54. The count probe assembly 100 of FIG. 14 can be used in place of the count probe 14 shown in FIG. 1. A description of the operation of probe 100 with such an apparatus will be described hereinafter. A detailed description of each of these members will now be given with reference to FIGS. 15–27.

Figure 15:
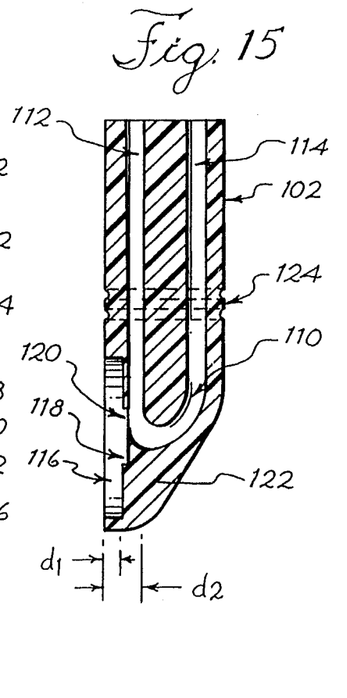
FIG. 15 illustrates a side cross-sectional view of a core member of the probe assembly shown in FIG. 14.

A core member 102 is illustrated in detail with reference to FIGS. 15–17. FIG. 15 illustrates a side cross-sectional view of the core member 102 of the probe assembly shown in FIG. 14. The core member 102 may be formed of a polymeric material, such as a molded acrylic and the like. A substantially "U" shaped conduit 110 is formed in the interior of the core member 102. Legs 112 and 114 of conduit 110 open at the top of the core member 102 (see FIG. 17). The legs 112 and 114 of conduit 110 align with conduits 76 and 72 respectively of base 12 (see FIGS. 7–9) when the probe assembly 100 of FIG. 14 is mounted to the base 12. The core member 102 contains a single, continuous conduit 110 as opposed to the conduit of the count probe 14 of FIGS. 2 and 3 which is formed only when the cap 28 is mounted to the end of the tube 26.

A recess 116 is formed in a lower portion of the core member 102. The recess 116 may be polygonal, preferably rectangular, in shape and extends into the core member 102 a distance $d_1$, which preferably measures about 0.057 inches. Formed in the center of recess 116 is a substantially circularly shaped recess 118. In an exemplary embodiment, the recess 118 has a diameter of about 0.173 inches and extends a distance $d_2$ of about 0.077 inches into the core member 102. The recess 118 is positioned to expose a portion of conduit 110 to the exterior of the core member 102. A substantially semi-circular shaped counterbore 120 (See FIG. 16), having a radius of preferably about 0.045 inches is formed by an intersection of recess 118 with the conduit 110. Two guiding slots 122 (shown in phantom in FIGS. 15-17) are formed on opposite sides of the interior of the core member 102. The guiding slots 122 mate with guiding tabs (not shown) formed on the sleeve member to positively position the core member 102 within the sleeve member. Grooves 124 are formed on the exterior of the core member 102 which help to secure the sleeve member to the core member 102 as will be described in detail hereinafter.

In the illustrated embodiment, the core member 102 has a length preferably of about 1.275 inches. The guiding slots 122 extend preferably about 0.45 inches from the bottom of the core member 102. Recess 116 has a width $w_1$ preferably of about 0.342 inches.

Figure 16:
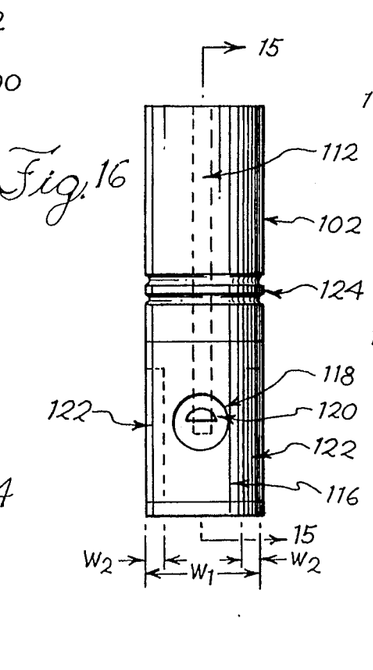
FIG. 16 illustrates a front view of the core member shown in FIG. 15.

FIG. 16 illustrates a front view of the core member 102 shown in FIG. 15. A substantially circular recess 118 is formed approximately at the center of recess 116 to form the substantially semi-circle shaped counterbore 120 exposing a portion of conduit 110 formed in the interior of the core member 102 to the exterior of the core member 102. The leg 112 of conduit 110 is shown in phantom and extends below counterbore 120. In the illustrated embodiment, guiding slots 122 extend a distance $w_2$, which measures preferably about 0.050 inches into the interior of the core member 102.

Figure 17:
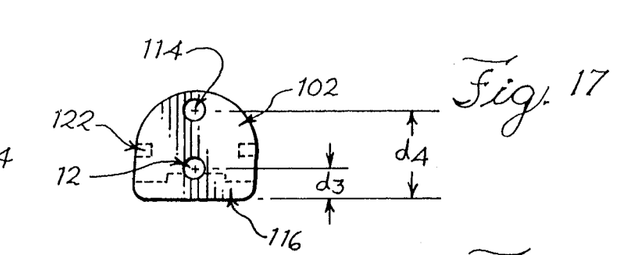
FIG. 17 illustrates a top view of the core member shown in FIG. 15.

FIG. 17 illustrates a top view of the core member 102 shown in FIGS. 15 and 16. Guiding slots 122 and recesses 116 and 118 are shown in phantom. Conduit 110 preferably has a diameter of about 0.060 inches. Leg 112 of conduit 110 is located preferably a distance $d_3$ of about 0.097 inches from a side of the core member 102 and leg 114 of conduit 110 is located a distance $d_4$ of preferably about 0.284 inches from the side of the core member 102.

Figure 18:
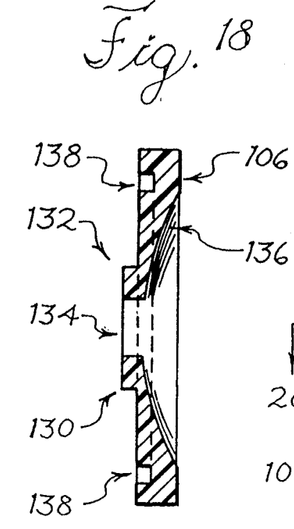
FIG. 18 illustrates a cross-sectional view of the count wafer plate shown in FIG. 14.

FIG. 18 illustrates a cross-sectional view of a count wafer plate 106 illustrated in FIG. 14. The wafer plate 106 is substantially polygonal, preferably rectangular, in shape with a projection 130 formed on a rear side 132 thereof. The projection 130 is dimensioned to fit within recess 118 formed in the core member 102. An aperture 134 is formed substantially at the center of the projection 132 and opens up into a substantially oval shaped aperture 136 at the front 138 of the wafer plate 106. As noted above, the count wafer plate 106 houses the count wafer 54. Thus, the apertures 134 and 136 are configured and disposed to substantially align with the aperture in the count wafer 54 when the count wafer 54 is assembled with the count wafer plate 106. In the illustrated embodiment, the aperture 134 has a diameter of about 0.082 inches. Also formed on the rear side 132 of the wafer plate 106 is a recess 138 shaped to accommodate an O-ring therein as will be described in detail hereinafter with reference to FIGS. 23 and 24.

Figure 19:
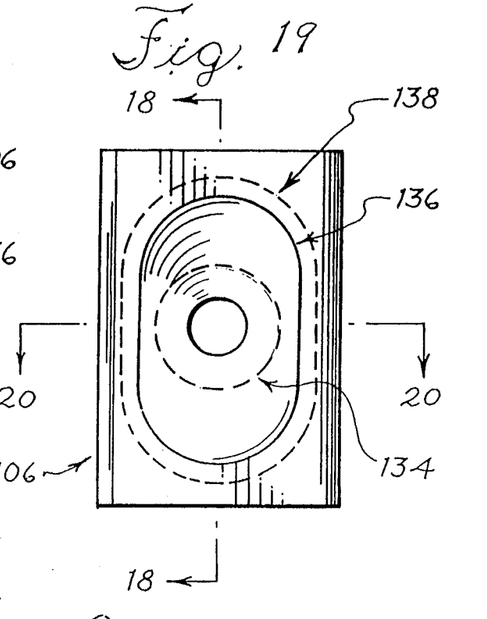
FIG. 19 illustrates a front view of the count wafer plate shown in FIG. 18.
Figure 20:
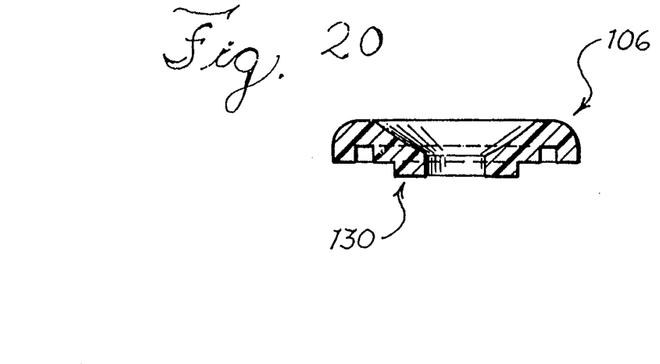
FIG. 20 illustrates a top cross-sectional view of the count wafer plate shown in FIG. 18.

FIG. 19 illustrates a front view of the count wafer plate 106 shown in FIG. 18. A recess 138 is formed substantially around the periphery of aperture 138. FIG. 20 illustrates a cross-sectional view of the count wafer plate 106.

Figure 21:
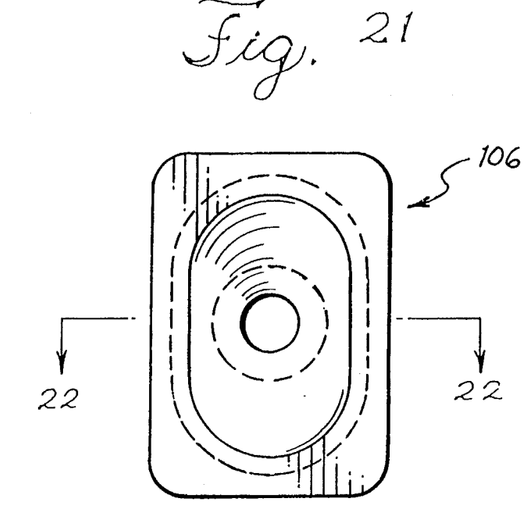
FIG. 21 illustrates a front view of an alternative count wafer plate.
Figure 22:
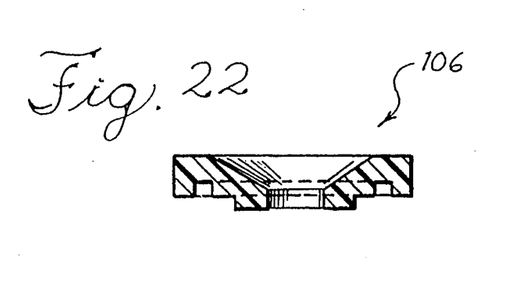
FIG. 22 illustrates a top cross-sectional view of the count wafer plate shown in FIG. 21.

FIGS. 21 and 22 illustrate an alternate embodiment of a count wafer plate 106 which may be used in conjunction with the probe assembly shown in FIG. 14. A cross-sectional view of the wafer plate 106 is substantially identical to that illustrated in FIG. 18. It is to be noted that the embodiment of the count wafer plate 106 illustrated in FIGS. 18 through 20 has substantially pointed edges whereas the embodiment of FIGS. 21 and 22 has substantially rounded edges.

Figure 23:
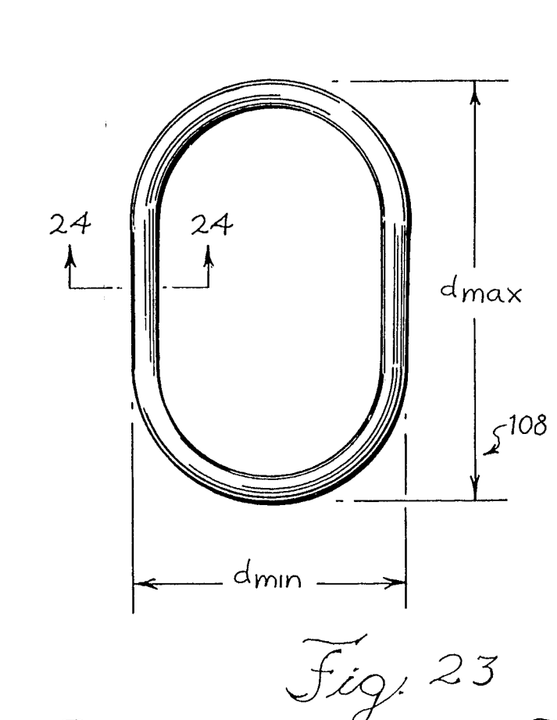
FIG. 23 illustrates a front view of the O-ring shown in FIG. 14.
Figure 24:
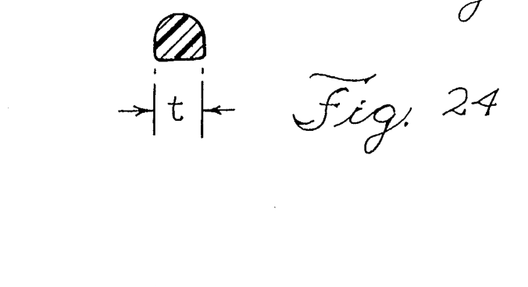
FIG. 24 illustrates a cross-section view taken along lines 24—24 of FIG. 23.

FIG. 23 is a front view of the O-ring 108 shown in FIG. 14. In the illustrated embodiment, the O-ring 108 has a maximum diameter ($d_{max}$) of about 0.440 inches and a minimum diameter ($d_{min}$) of about 0.282 inches. The O-ring 108 is preferably formed of an elastomeric material. FIG. 24 illustrates a latitudinal cross-section of a portion of the O-ring 108 shown in FIG. 23 taken along lines 24-24. In the illustrated embodiment, the O-ring 108 has a thickness t of about 0.025 inches. The O-ring 108 is dimensioned to fit within recess 138 formed in the count wafer plate 106. In particular, as illustrated in FIG. 24, one side of the O-ring 108 is substantially planar or flattened to fit within the recess 138 of the wafer plate 106, thereby leaving an arcuate surface exposed.

Figures 25, 26, 27:
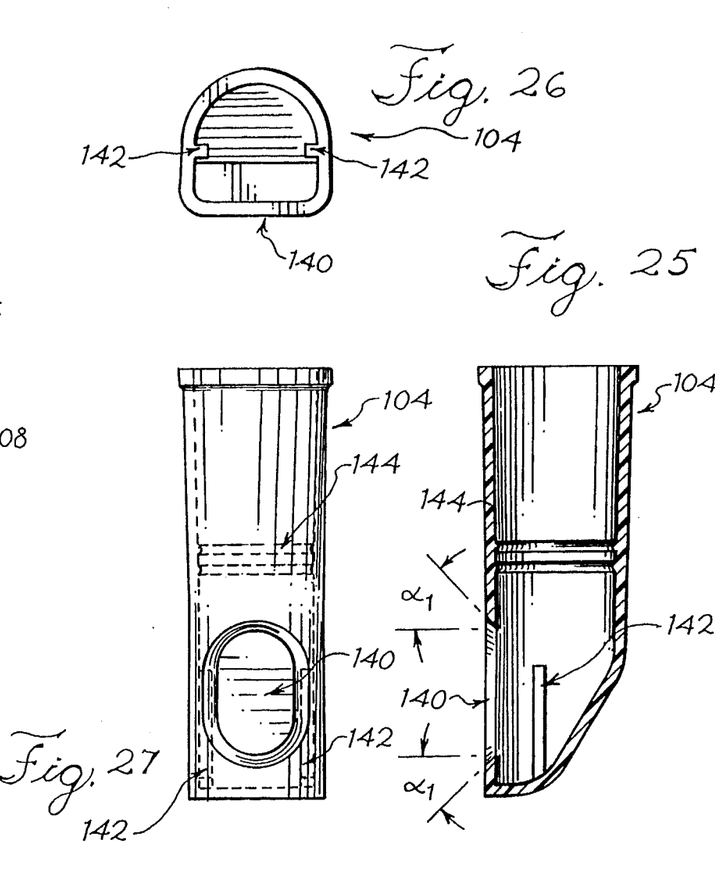
FIG. 25 illustrates a side cross-sectional view of the sleeve shown in FIG. 14.
FIG. 26 illustrates a top view of the sleeve shown in FIG. 25.
FIG. 27 illustrates a front view of the sleeve shown in FIG. 25.

FIG. 25 illustrates a cross-sectional view of the sleeve member 104. The sleeve member 104 is preferably molded of a polymeric material such as polymethyl pentane, another polyolefin and the like. As can be seen from FIGS. 25-27, the sleeve member 104 has substantially the same configuration as the core member 102. An aperture 140 is provided along a side of the sleeve member 104. The edges of the aperture 140 are preferably beveled at an angle $a_1$ of about 45°. As can best be seen in FIG. 26, guiding grooves 142 are formed on the interior opposite side walls of the sleeve member 104. As previously described, the guiding grooves 142 are appropriately dimensioned to fit in the guiding slots 122 (See FIGS. 15-17) of the core member 102. Also formed on the interior of the sleeve member 104 are grooves 144 which mate with the grooves 124 formed on the core member 102 to hold the sleeve member 104 in position with reference to the core member 102. In the illustrated embodiment, the sleeve member 104 is slightly shorter than the core member 102, having a length preferably measuring about 1.515 inches.

The assembly of the probe illustrated in FIG. 14 will now be described. The O-ring 108 is inserted in recess 138 of the count wafer plate 106. In some embodiments, a lubricous substance, such as a silicone grease and the like, may be applied to the O-ring 108 to augment a seal formed by the O-ring 108 and thereby preserve the desired sealing characteristics (i.e. current leakage). The count wafer plate 106 is then mounted on the core member 102 by inserting projection 130 of the wafer plate 106 into recess 118 of member 102. As is illustrated in FIG. 14, wafer plate 106 is mounted so that O-ring 108 abuts the core member 102. The sleeve 104 is then slid over the combination of the core member 102, wafer plate 106 and O-ring 108 until grooves 144 mate with grooves 124 or the core member 102 to hold the sleeve 104 in place.

As previously mentioned, the probe assembly 100 shown in FIG. 14 may replace the probe assembly 14 shown in FIG. 1. In one embodiment, the probe assembly 100 may be formed integrally with tile base 12. To mount the probe assembly 100 to base 12 as shown in FIGS. 1 and 7-10, conduit 110 must be aligned with the appropriate conduit of the base 12; leg 114 of conduit 110 must be aligned with conduit 72 in the base 12. The counting apparatus would operate in the same manner as described above with reference to FIGS. 1-13.

The probe assembly 100 of FIG. 14 offers several advantages. The sleeve 104 is removable along with the count wafer plate 106 and O-ring 108 to facilitate cleaning. Defective or worn elements can be replaced, and the count wafer plate containing a count wafer can be exchanged for a count wafer plate housing another count wafer having a different size aperture.

Figures 28, 29:
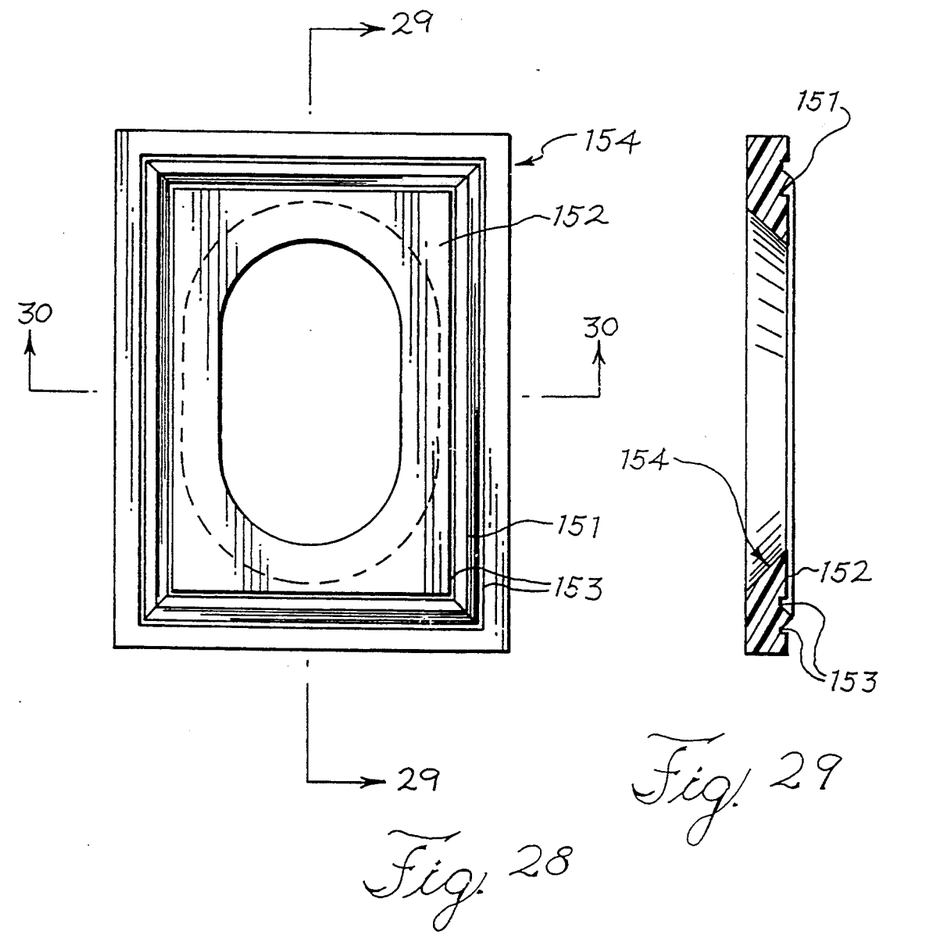
FIG. 28 is a rear view of a count wafer plate retention plate.
FIG. 29 is a sectional view, taken along line 29—29 of FIG. 28.
Figure 30:
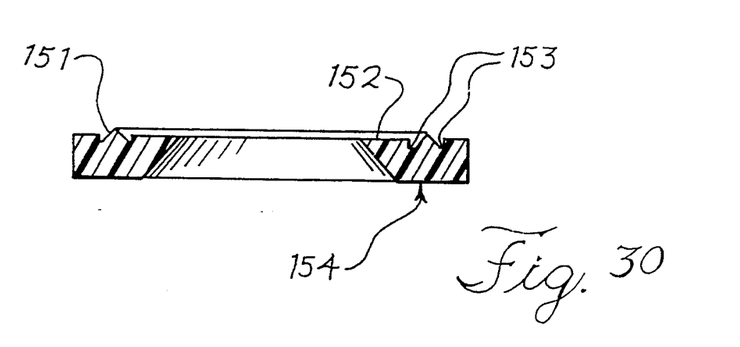
FIG. 30 is a sectional view, taken along line 30—30 of FIG. 28.

Drawing attention to FIGS. 28 through 30, yet another embodiment of the present invention will be described. This embodiment is substantially similar to the embodiments discussed above except for the differences to be detailed below.

This embodiment generally utilizes a retention member in the form of a count wafer retention plate 154, instead of the sleeve 104, to retain the count wafer 54 in operative association with a core member. The count wafer retention plate 154 is preferably made of a polymeric material, such as acrylic and the like, and is polygonal, preferably rectangular, in shape. The shape of the count wafer retention plate 154 preferably complements the shape of the count wafer plate 106.

The count wafer retention plate 154 comprises a facing side and an abutting side 152 which operatively engages a portion or periphery of the count wafer plate 106 when assembled. A rib 151 extends substantially around the entire periphery of the retention plate 154. The rib 151 is illustrated in the Figures as having a substantially pointed configuration, but other configurations are also possible. The rib 151 preferably defines a configuration which complements the configuration of the count wafer plate 106. Specifically, in the illustrated embodiment, the rib 151 defines a substantially rectangular configuration which complements the configuration of the count wafer plate 106 illustrated in FIG. 19. A recess 153 is disposed along at least one side of the rib 151. The recess 153 defines a level lower than a level defined by the abutting side 152.

The assembly of a probe including a count wafer retention plate 154 will now be described. The count wafer 54 is applied to the count wafer plate 106 as before. The count wafer plate 106, containing the count wafer 54, is added to the core member in the same manner as before. The retention plate 154 is positioned with respect to the count wafer plate 106 such that the count wafer plate 106 is disposed within the region defined by the rib 151. The retention plate 154 engages the core member. Alternatively, the count wafer plate 106 may be first applied to the count wafer retention plate 154 and then the combined plate assembly can be applied to the core member. The abutting side 152 of the retention plate 154 engages the count wafer plate 106 and the rib 151 engages the core member.

The retention plate 154 is now bonded to the core member. Preferably, this is done by ultrasonic welding or similar technique. If the retention plate 154 were ultrasonically welded to the core member, then the ultrasonic energy is directed such that at least a portion of the rib 151 becomes substantially molten. It is to be noted that the core member and the retention plate 154 are preferably formed of the same material, such as acrylic and the like, which facilitates ultrasonic welding. The molten material flows between the core member and the retention plate 154. Some of the material may flow into the recess 153. The ultrasonic energy is applied for a time sufficient to provide a firm bond between the retention plate 154 and the core member. The count wafer plate 106 housing the count wafer 54 is now firmly sandwiched between the retention plate 154 and the core member. It is to be remembered that while the count wafer may not be easily removed from the core member in some of the above-discussed embodiments of the invention, the core member itself may be provided as a removable and replaceable element of the probe assembly.

While embodiments of this invention have been shown and described in connection with the preferred embodiments, it is apparent that certain changes and modifications may be made from the basic features of the embodiments of the present invention. Accordingly, it is the intention of the Applicants to protect all variations and modifications within the true spirit and valid scope of the present invention.

What is claimed is:

1. A particle analyzer having a count probe capable of counting particles comprising:
   (a) a tube member having a connection end and two fluid passageways therein;
   (b) a removable cap having an interior mounted to the connection end of the tube, wherein the interior of the cap provides a connection between the two fluid passageways of the tube member to form one continuous passageway, said cap having a bore extending through a side wall thereof; and
   (c) a count wafer having an aperture dimensioned to fit in the bore formed in the side wall of the cap, wherein the wafer is held in the bore by forces exerted by the cap, the aperture of the wafer being positioned to align with the continuous passageway formed by the cap and tube.

2. A particle analyzer according to claim 1 wherein the cap is formed of a polymer.

3. A particle analyzer according to claim 2 wherein the polymer is a silicone.

4. A particle analyzer according to claim 1 wherein the connection end of the tube member includes a tip section having a groove therein, the tip section cooperating with the cap to form the continuous passageway between the groove and the interior of the cap.

5. A particle analyzer according to claim 4 wherein the aperture of the count wafer mounted in the bore of the cap is located no more than about 0.020 inches from the groove in the tip section of the tube.

6. A particle analyzer having a count probe for counting particles comprising:
   (a) a core member having a fluid passageway formed therein and a recess formed on one side so as to expose a portion of the fluid passageway;
   (b) a wafer having an aperture dimensioned to fit within the recess of the core member so that the aperture exposes a portion of the fluid passageway; and
   (c) a sleeve member removably mounted over the core member and the wafer mounted therein to hold the wafer in place, the sleeve member having an aperture in one side which, when the sleeve member is mounted over the core member and the wafer, aligns with the aperture in the wafer.

7. A particle analyzer according to claim 6 wherein the sleeve member is formed of a polymer.

8. A particle analyzer according to claim 7 wherein the polymer is a polyolefin.

9. A particle according to claim 6 wherein the fluid passageway formed in the core member is substantially U-shaped.

10. A count probe comprising:
    (a) a member having a conduit and an opening;
    (b) a wafer including an aperture, wherein the wafer is dimensioned with respect to the opening such that the wafer is removably retained within the opening by an interference fit between the wafer and the member.

* * * * *